(12) United States Patent
Cinader, Jr. et al.

(10) Patent No.: US 7,993,133 B2
(45) Date of Patent: Aug. 9, 2011

(54) DIGITAL ORTHODONTIC TREATMENT PLANNING

(75) Inventors: David K. Cinader, Jr., Walnut, CA (US); Richard E. Raby, North St. Paul, MN (US); Nicholas A. Stark, Cottage Grove, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1000 days.

(21) Appl. No.: 11/551,372

(22) Filed: Oct. 20, 2006

(65) Prior Publication Data

US 2008/0096151 A1      Apr. 24, 2008

(51) Int. Cl.
*A61C 3/00*      (2006.01)

(52) U.S. Cl. .......................................... 433/24
(58) Field of Classification Search .................... 433/24; 700/98; 382/128, 154, 291
See application file for complete search history.

(56) References Cited

U.S. PATENT DOCUMENTS

| | | |
|---|---|---|
| RE35,169 E | 3/1996 | Lemchen et al. |
| 6,227,850 B1 | 5/2001 | Chishti et al. |
| 6,616,444 B2 | 9/2003 | Andreiko et al. |
| 6,632,089 B2 | 10/2003 | Rubbert et al. |
| 6,664,986 B1 | 12/2003 | Kopelman et al. |
| 6,739,869 B1 | 5/2004 | Taub et al. |
| 6,971,873 B2 | 12/2005 | Sachdeva et al. |
| 2004/0073417 A1 | 4/2004 | Rubbert et al. |
| 2004/0209220 A1* | 10/2004 | Manemann et al. ............ 433/24 |
| 2005/0130095 A1 | 6/2005 | Raby et al. |
| 2005/0170309 A1 | 8/2005 | Raby et al. |
| 2006/0024637 A1 | 2/2006 | Raby et al. |
| 2006/0073436 A1* | 4/2006 | Raby et al. ....................... 433/24 |
| 2006/0263740 A1* | 11/2006 | Sporbert et al. ................ 433/24 |

FOREIGN PATENT DOCUMENTS

KR      1020020072318      9/2002

* cited by examiner

*Primary Examiner* — Todd E Manahan
*Assistant Examiner* — Matthew M Nelson

(57) ABSTRACT

A digital orthodontic treatment planning system provides a practitioner with a digital representation of at least a part of a tooth of a patient within a three-dimensional environment. The practitioner may provide input indicative of a desired movement for a tooth of a patient via a user interface. Based on the desired movement for the tooth, a position of a virtual orthodontic appliance is calculated. The digital representation of the tooth may be moved in accordance with the adjusted position of the virtual orthodontic appliance. In this way, the system provides the practitioner with the perception that the input is being directly applied to the tooth, whereas the input is being indirectly applied to the tooth.

31 Claims, 5 Drawing Sheets

DIGITAL ORTHODONTIC TREATMENT PLANNING

TECHNICAL FIELD

The invention relates to orthodontics, and more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, which are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

A position of the bracket on a tooth as well as the interaction between the bracket and an archwire affects a resulting position of the tooth. As can be appreciated, it is important for the practitioner using straight wire appliances to precisely fix each bracket in the proper position on the corresponding tooth in order to achieve the desired tooth movement. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal directions, the resultant tooth orientation will likely be an orientation that is excessively rotated about its long axis.

The process of positioning and bonding the brackets to the patient's teeth often requires a practitioner to visually determine the proper location of the brackets on the respective teeth based on an estimate of how the brackets will affect the movement of the teeth. There is typically no way to confirm whether the selected bracket placement will result in the desired tooth movement. Similarly, there is typically no way to select a desired position for a tooth and subsequently select the location of a bracket on the tooth based on the desired position of the tooth.

The state of the art in orthodontics is rapidly moving toward digital and computer-aided techniques. These techniques include the use of intra and extra-oral scanners, three-dimensional (3D) modeling of a tooth structure, and fabrication of orthodontic appliances from digital data.

SUMMARY

In general, the invention relates to computer-implemented techniques for assisting practitioners in orthodontic diagnosis and treatment. More specifically, a computing system is described that provides an environment for modeling and depicting a digital representation of one or more teeth of a patient within a three-dimensional (3D) environment in order to develop an orthodontic treatment plan for achieving a desired functional and/or aesthetic arrangement of teeth. In some embodiments, the computing system also depicts a digital representation of an orthodontic appliance, such as a bracket. The digital representation of the orthodontic appliance may be an analog of the orthodontic appliance, a transparent or semi-transparent orthodontic appliance, a visible graphical representation or outline of the orthodontic appliance or an object indicative of the orthodontic appliance or indicative of one or more features of the orthodontic appliance.

By interacting with the system, an orthodontic practitioner is able to visualize the 3D representation of the dental arch, indicate a desired position or desired movement for one or more teeth, and determine a position of one or more orthodontic appliances that will result in the desired tooth position. The computing system allows a practitioner to interact with a 3D environment in order to indicate a desired position for a given tooth or a desired movement for the tooth. As explained in further detail below, the system implements certain techniques that provide the practitioner with the perception that he or she is directly manipulating the 3D representation of the patient's teeth so as to specify final (i.e., desired) tooth positions. However, in response to input from the practitioner, the computing system computes an adjustment to a current position of a bracket (or another orthodontic appliance). That is, instead of directly manipulating a tooth within the 3D environment (as the practitioner perceives) the movements input by the practitioner are instead applied to the appliance associated with the tooth, but in a reverse fashion. That is, the practitioner is unknowingly directly manipulating the appliance. The system then computes a new position for the tooth based on the adjustment to the appliance. In this manner, the movement and positioning of the tooth in the 3D environment is constrained to, and indeed calculated from, the orientation and behavior of the appliances associated with the teeth.

The extent to which the practitioner may indicate a desired movement for the tooth within the 3D environment is limited because when the practitioner is indicating a desired movement for a tooth, the practitioner is actually indicating a movement for the bracket associated with the tooth. Accordingly, the movement of the "tooth" by the practitioner within the 3D environment is constrained within geometric parameters in accordance with the simulated dental prescription, e.g., 3D models of the brackets and/or archwires that have been selected for the patient. The geometric parameters may be dictated by the behavior and/or geometry of the particular 3D model of the orthodontic appliance associated with the tooth or may be user specified.

In one embodiment, the invention is directed toward a computer-implemented method. The method includes rendering a digital representation of at least a portion of a tooth within a 3D environment, receiving input indicative of a desired movement for the tooth, calculating a new appliance position for a virtual appliance in response to the input instead of moving the tooth within the 3D environment in direct response to the input, calculating a new tooth position for the tooth based on the new appliance position of the virtual appliance, and rendering the digital representation of the tooth at the new tooth position within the 3D environment.

In another embodiment, the invention is directed toward a system comprising a computing device, and modeling software executing on the computing device. The modeling software comprises a rendering engine that renders a digital representation of at least a portion of a tooth within a 3D environment, a user interface to receive user input indicating a desired movement for the tooth, an orthodontic appliance control module to automatically calculate an orthodontic appliance position based on the input, and a tooth control module to move the tooth within the 3D environment in accordance with the orthodontic appliance position.

In yet another embodiment, the invention is directed toward a computer-readable medium. The computer-readable medium comprises instructions for causing a programmable processor to render a digital representation of at least a portion of a tooth within a 3D environment, render a virtual orthodontic appliance as a transparent or semi-transparent object within the 3D environment, receive input indicative of a desired movement for the tooth, calculate a new position for a virtual appliance in response to the input, and calculate a new position for the tooth within the 3D environment based on the new position of the virtual orthodontic appliance, and display the digital representations of the tooth and the virtual orthodontic appliance at their respective new positions.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
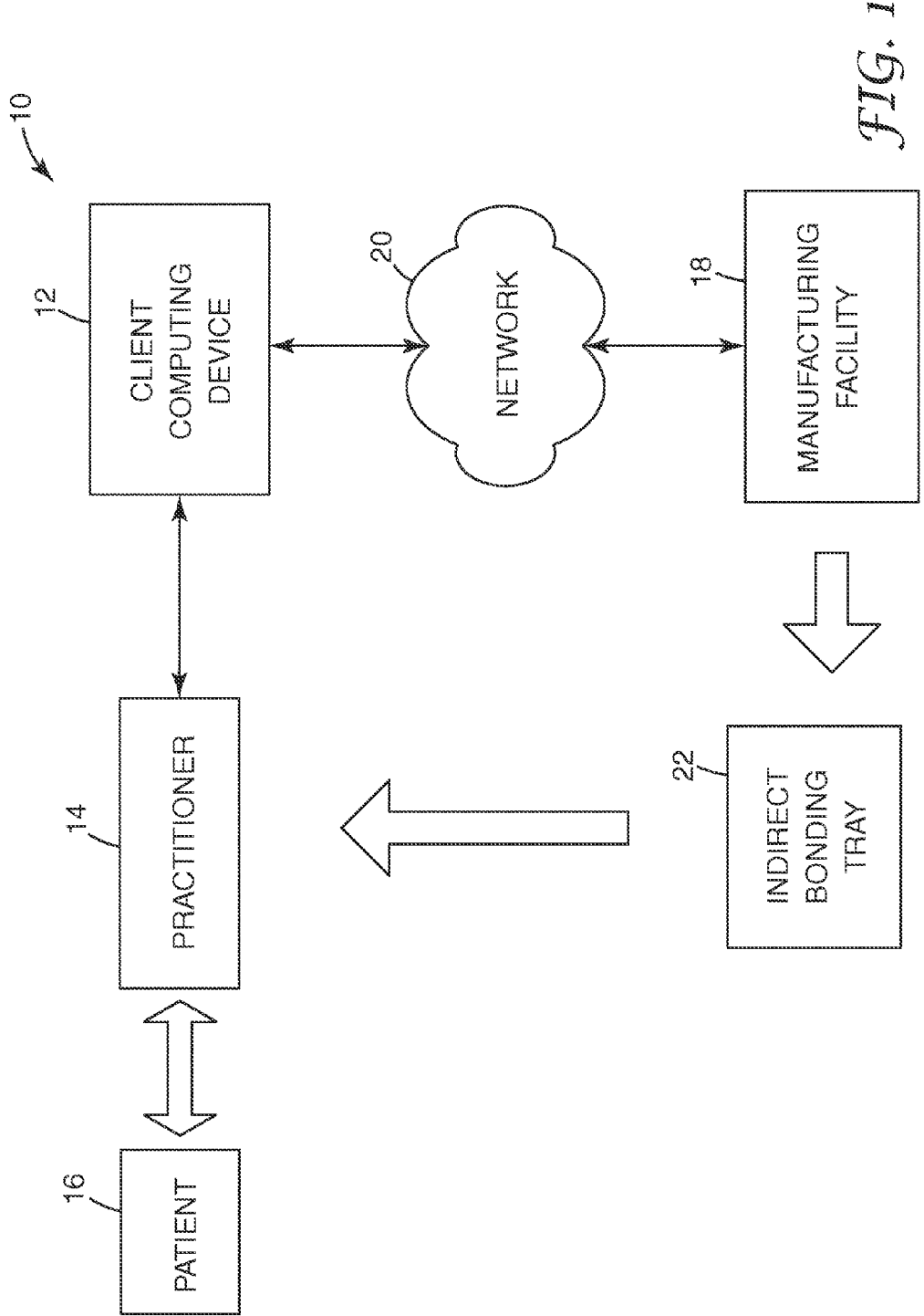
FIG. 1 is a block diagram illustrating an exemplary computer environment in which a client computing device receives an indication of a desired tooth position and/or desired tooth movement for generating an orthodontic treatment plan for a particular patient.

FIG. 1 is a block diagram illustrating an exemplary computer environment 10 in which client computing device 12 presents an environment for orthodontic practitioner 14 to interact with a digital representation of a portion of or an entire dental arch of patient 16 to generate and visualize an orthodontic treatment plan for patient 16. The orthodontic industry has developed standard prescriptions for many commercially available orthodontic appliances, In general, a prescription may set forth characteristics of one or more appliances, or a set of appliances. For example, the characteristics for a bracket may include torque, angulation, labial-lingual offset (in-out) and rotational offset. For some patients, a standardized set of metrics for the teeth in the dentition may satisfy the functional and aesthetic requirements. For other patients, practitioner 14 may desire to create a customized prescription to achieve a more aesthetically pleasing result, or to more adequately take into account that patient's malocclusion. As another example, a combination of standardized and customized prescriptions for different teeth in the dentition may be used. Practitioner 14 may formulate a customized prescription using modeling software client computing device 12.

As described herein, client computing device 12 provides an intuitive interface for practitioner 14 to indicate desired positions for one or more teeth and realize an orthodontic treatment plan (e.g., bracket placement) for achieving the desired tooth positions. In particular, client computing device 12 provides an interface that provides practitioner 14 with a perception that he or she is directly manipulating the 3D representation of teeth of patient 16 to specify desired tooth positions. However, client computing device 12 translates the movement indicated by practitioner 14 with respect to a selected tooth (or more than one tooth) to movement of an orthodontic appliance associated with the selected tooth, and recalculates a position of the orthodontic appliance accordingly. Client computing device 12 may then calculate and move the selected tooth based on the recalculated position of the orthodontic appliance. In this way, practitioner 14 perceives that he or she is directly moving the teeth, but is in fact indirectly moving the teeth by first indicating a desired movement for an orthodontic appliance.

The term "movement" generally refers to the overall movement of a particular tooth from a first position to a second position, rather than the path (e.g., a curved path) the particular tooth traverses to move from the first position to the second position. Thus, when practitioner 14 provides input to client computing device 12 indicative of a desired movement for a tooth, practitioner 14 need only specify a second position for the tooth, rather than specifying the entire path along which the tooth should move. Based on the inputted movement from practitioner 14, client computing device 12 applies the movement to the bracket and then automatically calculates a resultant path the particular tooth traverses in the 3D environment to move the tooth from the first position to approximately the second position indicated by practitioner 14. In the description below, the phrases "desired movement" and "desired position" are used interchangeably because it is understood that when practitioner 14 indicates a desired position for a particular tooth, practitioner 14 incidentally indicates a desired movement for the tooth. The converse likewise applies. That is, when practitioner 14 indicates a desired movement for a particular tooth, practitioner 14 is incidentally indicating a desired position for the tooth.

Although the description will generally discuss the display and positioning of one or more teeth and orthodontic brackets, it shall be understood that client computing device 12 may display and/or position any type of orthodontic appliance without departing from the scope of the present invention. Examples of such orthodontic appliances include, but are not limited to, orthodontic brackets, buccal tubes, sheaths or buttons.

Client computing device 12 displays a digital representation of one or more teeth within a three-dimensional (3D) environment. For example, client computing device 12 may display a digital representation of a portion of or an entire dental arch of a patient. The digital representation of the teeth may be initially generated by digitally scanning a physical dental impression of the teeth of patient 16, or by scanning a casting made from the impression. Alternatively, practitioner 14 may use an intraoral scanner to produce the digital representation directly from the teeth of patient 16. Other methods of scanning or otherwise obtaining a digital representation of the teeth are also possible.

Client computing device 12 may also display a digital representation of one or more orthodontic appliances associated with the teeth. In one embodiment, the orthodontic appliance is a bracket. However, in other embodiments, the orthodontic appliance may be any appliance that corresponds to a particular tooth of patient 16, or a particular set of teeth, where a set is generally less than a full dental arch of patient 16. Client computing device 12 need not display a full visual representation of an orthodontic appliance. Rather, a portion of the appliance may be displayed, such as an outline of the appliance or an outline of certain features of the appliance. In addition, client computing device 12 may display a full visual representation of an archwire or alternatively, a portion of an archwire, such as an outline of the archwire or an outline of certain features of the archwire. The orthodontic appliance and/or archwire may be displayed as a visible object or partially visible object or alternatively, the appliance may be displayed as a transparent object for clarity of illustration of the teeth to further provide an interface in which practitioner 14 perceives he or she is arranging the teeth directly rather than the orthodontic appliance(s).

As another alternative, client computing device 12 need not display the appliance itself. Rather, another object associated with an appliance or with the placement of an appliance may be shown instead of or in addition to the appliance itself. Examples of such other objects include crosshairs (intersecting lines indicating the position on a tooth where the center of an appliance is to be placed), placement jigs, placement guides, or other objects which may represent or be attached to an appliance, or which may be otherwise associated with an appliance and/or its placement. Alternatively, client computing device 12 may reference an orthodontic appliance analog (i.e., an orthodontic appliance represented by data, such as a coordinate system) instead of the device itself. The terms "appliance" or "bracket" as used herein shall therefore be understood to include any type of appliance, a full or partial representation of an appliance, any object associated with an appliance and/or its placement or an analog of the orthodontic appliance.

As described in detail herein, client computing device 12 presents a graphical user interface (GUI) with which practitioner 14 interacts to define a prescription for patient 16. Client computing device 12 controls the GUI to operate in one of two modes. In a first mode, practitioner 14 interacts with the GUI presented by client computing device 12 to view the digital representation of the teeth within the 3D environment, define a proposed orthodontic prescription, and determine the proper placement of one or more brackets with respect to one or more teeth for achieving a desired functional and/or aesthetic result. That is, practitioner 14 selects virtual brackets and directly manipulates the virtual brackets within the 3D environment to position the brackets on individual teeth within the modeled dental arch. To aid the practitioner, client computing device 12 may initially place the virtual brackets on individual teeth based on standard prescriptions for commercially available brackets or an initial prescription specified by practitioner 14. Practitioner 14 may then adjust the position of a particular bracket on a particular tooth to achieve a desired functional and/or aesthetic result. Client computing device 12 then computes the placement of the modeled teeth resulting from the initial bracket placement, and subsequently, the direct manipulation of the brackets by practitioner 14.

In a second mode, client computing device 12 controls the user interface of the 3D environment so that practitioner 14 perceives that he or she is directly manipulating individual teeth so as to specify final tooth positions. For example, client computing device 12 may render the brackets transparently, semitransparently or invisibly so that practitioner 14 may perceive that input is being applied to directly position the teeth in the 3D environment. In fact, however, client computing device 12 receives, via the user interface, input specifying movements (e.g., by way of a mouse or other pointing device), effectively reverses the movements within the 3D environment, and applies the movements to the brackets. In this manner, in the second mode practitioner 14 is unknowingly directly manipulating the virtual brackets, which may be invisible, rendered transparently or rendered as visible objects on the GUI. Client computing device 12 then computes a new position for the tooth within the 3D environment based on the adjustment to the bracket. Thus, the movement and positioning of the tooth in the 3D environment is constrained to, and indeed calculated from, the orientation and behavior of the appliances associated with the teeth. As such, the techniques allow practitioner 14 to interact with the GUI presented by client computing device 12 with the perception that he or she is precisely locating the finish positions (i.e., post-treatment positions) of each tooth within the 3D environment. In either mode, computing device 12 provides a user interface that allows practitioner 14 to adjust a relative tooth-bracket position.

Although client computing device 12 effectively moves the virtual brackets and computes tooth positions in the same manner for each of the two modes, the second mode may provide a more intuitive and/or easier interface for some practitioners than the first mode. The first mode requires the practitioners to iteratively move brackets so as to achieve the desired tooth positions with the understanding that moving a bracket in one direction on a tooth tends to move that tooth in the opposite direction during treatment. Although the practitioner is effectively moving the virtual brackets in the same manner in the second mode, this may be more intuitive to the practitioner since he or she can specify movements in the same direction he or she wishes to move a given tooth and client computing device 12 reverses the movement and applies it to the corresponding appliance.

Once a proposed orthodontic prescription is formulated and displayed, the orthodontic appliances are placed to achieve a final functional and/or aesthetic result, and practitioner 14 has indicated his or her approval, client computing device 12 communicates the bracket placement positions to manufacturing facility 18 via network 20. In response, manufacturing facility 18 constructs an indirect bonding tray 22 for use in physically placing brackets on the teeth of patient 16. In other words, manufacturing facility 18 fabricates indirect bonding tray 22 based on the bracket placement positions selected by practitioner 14 within the 3D environment presented by client computing device 12. Manufacturing facility 18 may, for example, use conventional commercially available brackets selected by practitioner 14 to form indirect bonding tray 22. Manufacturing facility 18 forwards indirect bonding tray 22 to practitioner 14 for use in a conventional indirect bonding procedure to place the brackets on the teeth of patient 16. As another option, manufacturing facility 18 constructs a custom jig for placing a single bracket on patient's 16 tooth or a group of brackets on, e.g., a quadrant of a dental arch or an entire dental arch instead of the indirect bonding tray 22.

Alternatively, client computing device 12 need not forward the bracket placement positions to manufacturing facility 18.

Client computing device 12 may instead output, e.g., display or print, the relevant distances and angles for each bracket to assist practitioner 14 in manually positioning the brackets on the teeth of patient 16. Alternatively, client computing device 12 may print a 2D representation of the 3D images displayed on the graphical user interface of client computing device 12.

Figure 2:
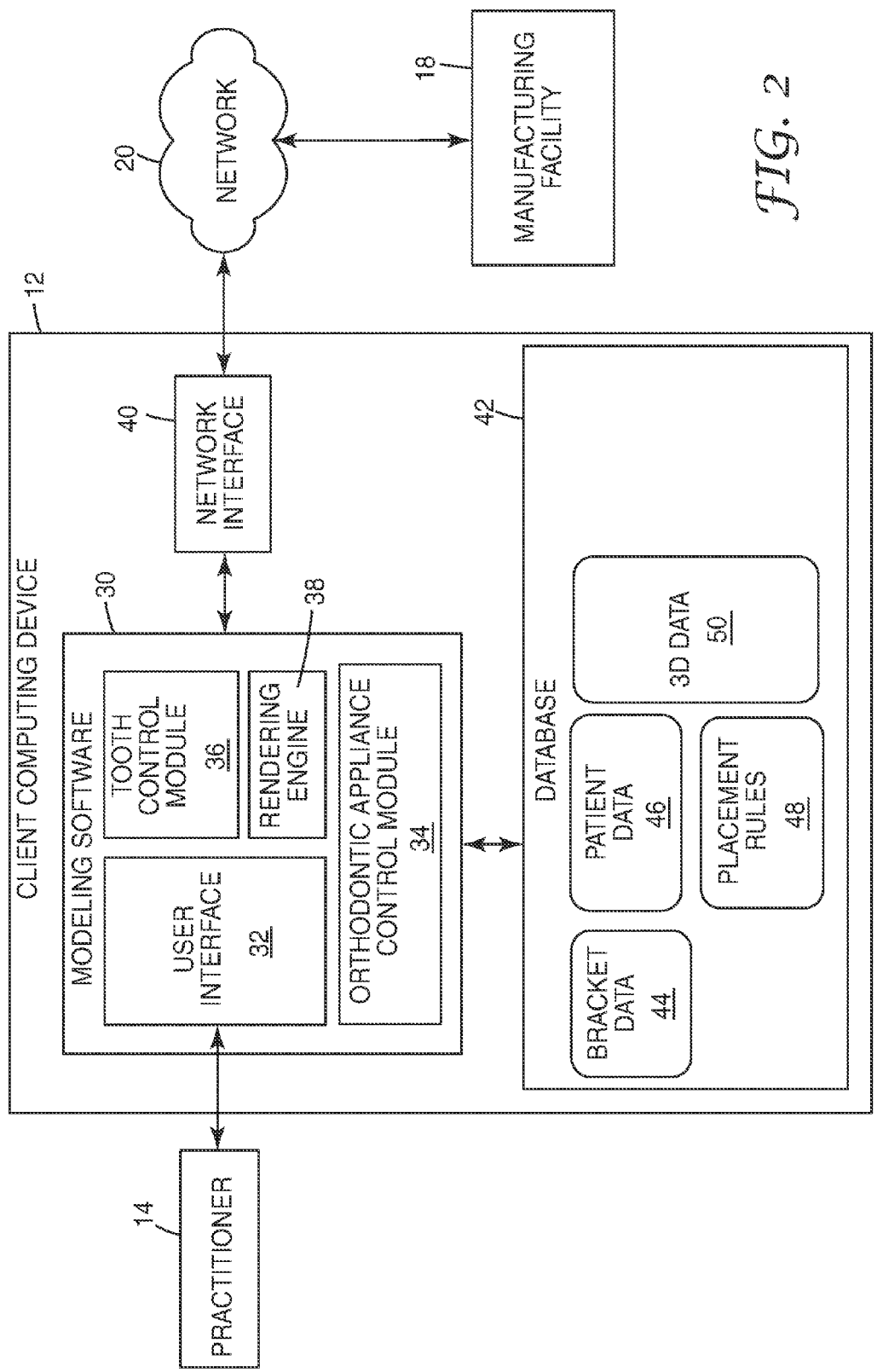
FIG. 2 is a block diagram illustrating an example embodiment of client computing device in further detail.

FIG. 2 is a block diagram illustrating an example embodiment of client computing device 12 in further detail. In the illustrated embodiment, client computing device 12 provides an operating environment for modeling software 30. As described above, modeling software 30 presents a modeling environment for modeling and depicting the 3D representation of the teeth of patient 16 (FIG. 1). In the illustrated embodiment, modeling software 30 includes a user interface 32, an orthodontic appliance control module 34, tooth control module 36, and rendering engine 38. Modeling software 30 interfaces with network 20 via network interface 40.

User interface 32 provides a GUI that visually displays the 3D digital representation of the patient's teeth as well as 3D digital representations of the brackets (or other orthodontic appliance). In addition, user interface 32 provides an interface for receiving input from a user, such as practitioner 14, e.g., via a keyboard and a peripheral device, for manipulating a tooth or bracket. User interface 32 may also visually display a 3D representation of the patient's dental arch and/or of specified portions of the patient's dental arch. In other embodiments, user interface 32 may display a two-dimensional (2D) representation of the patient's dental arch and/or of specified portions of the patient's dental arch.

Orthodontic appliance control module 34 and tooth control module 36 may be considered interactive modules for developing an orthodontic treatment plan for achieving a desired tooth arrangement for a particular patient 16 (FIG. 1). Practitioner 14 may interact with modeling software 30 via user interface 32 to indicate a desired movement for a particular tooth. After practitioner 14 indicates the desired movement, orthodontic appliance control module 34 translates and applies the inputted movement to calculate a new position of a bracket associated with the particular tooth. Orthodontic control module 34 may also move the bracket based on the translated movement. In embodiments in which a digital representation of the bracket is rendered and displayed on user interface 32, the adjusted position of the bracket may be displayed on user interface 32.

As described above, during treatment, moving a bracket in one direction generally results in movement of the tooth associated with the bracket in an opposite direction. Thus, in one embodiment, orthodontic appliance control module 34 translates the desired tooth movement to movement of the bracket by reversing the direction of desired movement inputted by practitioner 14. Orthodontic appliance control module 34 reverses the desired tooth movement when applying the movement to the bracket in order to move the bracket in a direction that will result in tooth movement substantially close to the desired tooth movement indicated by practitioner 14. In this way, practitioner 14 is actually inputting movements for the bracket instead of the tooth. However, modeling software 30 provides an interface in which practitioner 14 perceives that he or she is directly moving a tooth within the 3D environment because subsequent to calculating the adjusted position of the bracket, tooth control module 36 then calculates a new position for the tooth based on the adjusted position of the bracket and moves the tooth accordingly. Tooth control module 36 may move teeth based on the adjusted position of the bracket according to a set of tooth-bracket rules. Each tooth and respective bracket pair is governed by a set of rules, whereby movement of the tooth results in a corresponding movement of the respective bracket or vice versa. The tooth-bracket rules may be stored within database 42. Tooth control module 36 may then move the digital representation of the tooth to the new position after orthodontic appliance control module 34 calculates an adjusted position of the bracket. In this way, the input by practitioner 14 indicative of a desired tooth movement indirectly moves the tooth. Tooth control module 36 may also automatically move affected teeth in the dental arch and orthodontic appliance control module 34 may automatically move affected brackets as a consequence of the movement of the selected tooth and bracket, respectively.

In one embodiment, the calculation of an adjusted position of a bracket by orthodontic appliance module 34 and the movement of the tooth by tooth control module 36 in accordance with the adjusted position of the bracket take place in real time, to further provide an environment in which practitioner 14 believes he or she is directly moving the tooth. That is, because this process is typically performed in real time by client computing device 12, the tooth appears to move directly after practitioner 14 indicates a desired movement for the tooth.

Modeling software 30 may receive an input indicative of a desired position for a tooth in multiple different ways. For example, as previously described, user interface 32 may visually display the 3D representation of the tooth. In one embodiment, practitioner 14 may left click on the digital representation of the tooth with a peripheral device (e.g., a mouse) and drag the tooth to the desired position in order to indicate the desired position and/or desired movement. Incremental movements of the peripheral device may correspond to defined movements within the 3D environment. As described above, in one mode of modeling software 30, practitioner 14 is actually indicating a desired movement for a bracket associated with the tooth when practitioner 14 indicates a desired movement for a tooth. Accordingly, modeling software 30 may be configured such that when practitioner 14 clicks and drags the tooth to the desired position, practitioner 14 is actually clicking and dragging a bracket (which may or may not be displayed on user interface 32), rather than the tooth itself. Orthodontic appliance control module 34 may then receive the input and reverse the input prior to calculating a new position of the bracket. In this way, practitioner 14 may indicate a desired position for a selected tooth by indicating a desired position for a bracket corresponding to the selected tooth while practitioner 14 is still under the impression that that he or she is moving the selected tooth itself rather than the bracket.

Alternatively, modeling software 30 may be configured such that when practitioner 14 clicks and drags the tooth to the desired position, practitioner 14 is not actually clicking and dragging any particular object within the 3D environment, but is indicating a desired movement having magnitude and directional components. In either embodiment, the incremental movements of the peripheral device are received by orthodontic appliance control module 34 and translated to define a movement value for the bracket within the 3D environment. In each of these embodiments, however, modeling software 30 supports the perception that practitioner 14 is directly moving a tooth because orthodontic appliance control module 34 calculates (and moves, if desired) an adjusted position of the bracket based on the movement indicated by practitioner 14, and tooth control module 36 moves the tooth in accordance with the adjusted position of the bracket in real time. That is, after practitioner 14 clicks and drags a tooth, the tooth appears to move in response to the input by practitioner 14, whereas modeling software 30 actually moves the tooth after calculating the adjusted bracket position in response to the input.

Alternatively, practitioner 14 may select a bracket number or tooth number from a selection menu, or by any other suitable means of selecting an object, and indicate a desired position of the selected tooth by inputting coordinate values for the desired position or inputting directional values that indicate the desired movement of the tooth.

User interface 32 may include navigational controls for moving and/or positioning the orthodontic object, such as by clicking on an icon that displays navigational controls for moving a virtual tooth and/or bracket. The result is that client computing device 12 allows practitioner 14 to interactively create a treatment plan for a patient by precisely positioning virtual teeth within a 3D environment and predicting the proper bracket placement for each tooth.

When practitioner 14 indicates a desired movement for a selected tooth, orthodontic appliance control module 34 and tooth control module 36 constrain the available movement within the 3D environment within geometric parameters. In particular, because practitioner 14 is actually indicating movement of a bracket (or other orthodontic appliance), orthodontic appliance control module 34 only receives input that is consistent with the behavior of the bracket within the 3D environment. For example, the input indicative of the desired movement for the tooth may be constrained within geometric parameters determined by an archwire using a straight-wire concept. Methods other than the straight wire concept may also be used. In one embodiment, the archwire is preselected by practitioner 14. The geometric parameters determined by an archwire may include, for example, parameters constraining the inputted movement to movement along the archwire (i.e., in the mesial-distal direction), movement generally perpendicular to the archwire (i.e., in the occlusal-gingival direction), and/or rotation generally about a labial-lingual axis.

Alternatively, the input may be constrained to movement along a 3D coordinate system that is based on a shape of a bracket. For example, the coordinate system may be curved in substantially the same way a bracket is curved, and as a result, practitioner 14 may only indicate a desired position for the tooth that is along the curved coordinate system. In this embodiment, the geometric parameters for the movement are determined by the shape of the bracket and may include a mesial-distal translation component, an occlusal-gingival translation component, and a rotational component about a labial-lingual axis. Given the varying shapes of teeth, the reference to an x-axis and z-axis is not a reference to strictly orthogonal x-y-z axes. Rather, the x-y-z axes associated with a tooth can only be generalized as generally orthogonal x-y-z axes.

Alternatively or in combination with the previous embodiments, orthodontic appliance control module 34 may limit the extent to which practitioner 14 may indicate a desired movement for a tooth based on geometric parameters determined by the relationship between the tooth and bracket. For example, it may be preferable for the digital representations of the bracket and tooth to be in snug and complementary contact with one another within the 3D environment, just as a back or base surface of a bracket typically contacts a labial surface of a tooth when the bracket is installed in a mouth of a patient. Thus, orthodontic appliance control module 34 may not allow practitioner 14 to input movements indicative of a desired tooth movement that are in directions and magnitudes that would result in a situation in which the bracket no longer contacts the tooth. In addition, orthodontic appliance control module 34 may not allow practitioner 14 to input movements that would result in a bracket penetrating a tooth. Similarly, orthodontic appliance control module 34 may not allow practitioner 14 to input movements that would result in a bracket becoming distinctly separated or too far displaced from its associated tooth. If practitioner 14 indicates a desired movement for a tooth outside of the geometric parameters, orthodontic appliance control module 34 may reject the input or may move the bracket in accordance with the input from practitioner 14 to the extent possible within the geometric parameters.

In some embodiments, a digital representation of the orthodontic appliance is rendered by rendering engine 38 and displayed on user interface 32 as either a visible object or a substantially transparent object (e.g., an outlined object, a partially outlined object or an opaque object), while in other embodiments, a digital representation of the orthodontic appliance is not displayed on user interface 32. In embodiments in which a 3D representation of the orthodontic appliance is not rendered and displayed on user interface 32, orthodontic appliance control module 34 may calculate an adjusted position of an analog of the orthodontic appliance (e.g., an orthodontic appliance represented by data, such as coordinates or behavior rules) in response to the input from practitioner 14. Therefore, reference to an orthodontic appliance may include a digital representation of the orthodontic appliance within the 3D environment and/or an analog of the orthodontic appliance.

As described above, modeling software 30 may also include another mode in which practitioner 14 may interact with user interface 32 to indicate a desired position for a bracket rather than a tooth. In this mode, practitioner 14 may input data indicating a desired movement for a particular orthodontic appliance via user interface 32. The orthodontic appliance is displayed as a visible object in the second mode. For example, in this mode, practitioner 14 may left click on the digital representation of the bracket and drag the bracket to the desired position in order to indicate the desired position and/or desired movement for the bracket. Alternatively, practitioner 14 may select a bracket number from a drop-down or other menu, or by any other suitable means of selecting an object. Practitioner 14 may also indicate a desired position for the bracket by inputting data relating to the desired magnitude and direction of movement of the bracket within the 3D environment.

Modeling software 30 interacts with database 42 to access a variety of data, such as bracket data 44, patient data 46, placement rules 48, and 3D data 50. Database 42 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS), object relational (ORDBMS) or other type of database management system. The data may, for example, be stored within a single relational database such as SQL Server from Microsoft Corporation. Although illustrated as local to client computing device 12, database 42 may be located remote from the client computing device 12 and coupled to the client computing device 12 via a public or private network, e.g., network 20.

Bracket data 44 describes a set of commercially available brackets or other orthodontic appliances that may be selected by practitioner 14 and positioned within the 3D modeling environment. For example, bracket data 44 may store a variety of attributes for the commercially available brackets, such as dimensions, slot locations and characteristics, torque angles, angulations and other attributes. User interface 32 may provide a menu-driven interface by which practitioner 14 selects the type of brackets for use in defining an orthodontic prescription for patient 16 (FIG. 1). Bracket data 44 may also include bracket-tooth behavior rules that define a relationship between each bracket and respective tooth.

Patient data 46 describes a set of one or more patients, e.g., patient 16 (FIG. 1), associated with practitioner 14. For example, patient data 46 specifies general information, such as a name, birth date, and a dental history, for each patient. Optionally, patient data 46 includes appointment scheduling information and billing information. In addition, patient data 46 specifies a current prescription specified for each of the patients, including the types of brackets selected by practitioner 14 for use with each of the patients, and their associated positions and orientations on the teeth of patient 14. After practitioner 14 determines a desirable bracket placement position via modeling software 30, practitioner 14 may store the bracket placement position within patient data 46 of database 42.

Placement rules 48 may specify industry-defined placement rules for commercially available orthodontic appliances. In addition, placement rules 48 may include user-defined rules specified by practitioner 14 or other rules for controlling appliance placement. Modeling software 30 and/or practitioner 14 (or a technician under the direction of practitioner 14) may reference placement rules 48 to initially place brackets or other orthodontic appliances with respect to one or more teeth of a patient prior to arranging teeth into a desired arch form.

One rule for certain commercially available brackets is to align the medial line or longitudinal axis of the bracket with the Facial Axis of the Clinical Crown (FACC) of the tooth. The FACC is defined as the curved line formed by the intersection of the mid-sagittal plane and the facial surface of the tooth. Another exemplary industry-defined placement rule is to place the center of a base of the bracket on the FACC of the tooth equidistant from the occlusal edge or occlusal-most point on the FACC and the gingival margin of the crown. This location is also known as the Facial Axis Point (FA Point). As another example, practitioner 14 may desire to place brackets at a position that is different from the FA Point. Consequently, practitioner 14 may specify different prescriptions for different types of teeth in the dentition, for different types of brackets, or both. Optionally, the prescription may be based in whole or in part on known rules associated with a particular type of the appliances selected by practitioner 14.

Rendering engine 38 accesses and renders 3D data 50 to generate the 3D view presented to practitioner 14 by user interface 32. More specifically, 3D data 50 includes information defining the 3D objects that represent each tooth and appliance within the 3D environment. Rendering engine 38 processes each object to render a 3D triangular mesh based on viewing perspective of practitioner 14 within the 3D environment. User interface 32 displays the rendered 3D triangular mesh to practitioner 14, and allows practitioner 14 to change viewing perspectives and manipulate objects within the 3D environment. If rendering engine 38 renders brackets, or any other orthodontic appliances, as transparent or visible objects, rendering engine 38 may initially place the brackets in the 3D environment using any of several different methods. For example, the brackets may initially be placed in the 3D environment using the method described in copending and commonly assigned U.S. Pat. No. 7,210,929, entitled "Method of Orienting an Orthodontic Appliance to a Tooth", filed Dec. 12, 2003 and issued on May 1, 2007 to Raby et al., which is incorporated herein by reference in its entirety. Manual adjustment of orthodontic brackets may be assisted by use of visual planar guides, as described in copending and commonly assigned U.S. Patent Application Publication No. 2005/0170309, entitled "Planar Guides to Visually Aid Orthodontic Appliance Placement within a Three-Dimensional (3D) Environment", filed Feb. 4, 2004 by Raby et al., which is incorporated herein by reference in its entirety. In that application, a system visually aids user placement of brackets through adjustments to bracket position and orientation.

Other methods of placing or adjusting the position of brackets on the teeth may also be used. For example, a system for automatic adjustment of an orthodontic appliance to a desired occlusal height is described in copending and commonly assigned U.S. Patent Application Publication No. 2006/0024637 entitled "Automatic Adjustment of an Orthodontic Bracket to a Desired Occlusal Height Within a Three-Dimensional (3D) Environment", filed Jul. 30, 2004 by Raby et al., which is incorporated herein by reference in its entirety. A system for placing teeth and/or brackets along an archwire is described in copending and commonly assigned U.S. Pat. No. 7,354,268, entitled "Movement of Orthodontic Objects Along An Archwire within a Three-Dimensional (3D) Environment," filed Apr. 6, 2006 and issued on Apr. 8, 2008 to Raby et al., which is incorporated herein by reference in its entirety.

It shall be understood that these and/or any other techniques may be used to initially place the orthodontic appliances on the teeth in the 3D environment and thus determine the patient's prescription, and that the invention is not limited in this respect. Moreover, although described for purposes of illustration with respect to modeling software 30 executing on client computing device 12, the techniques may be applied by any computing device, including servers remote from practitioner 14.

Figure 3:
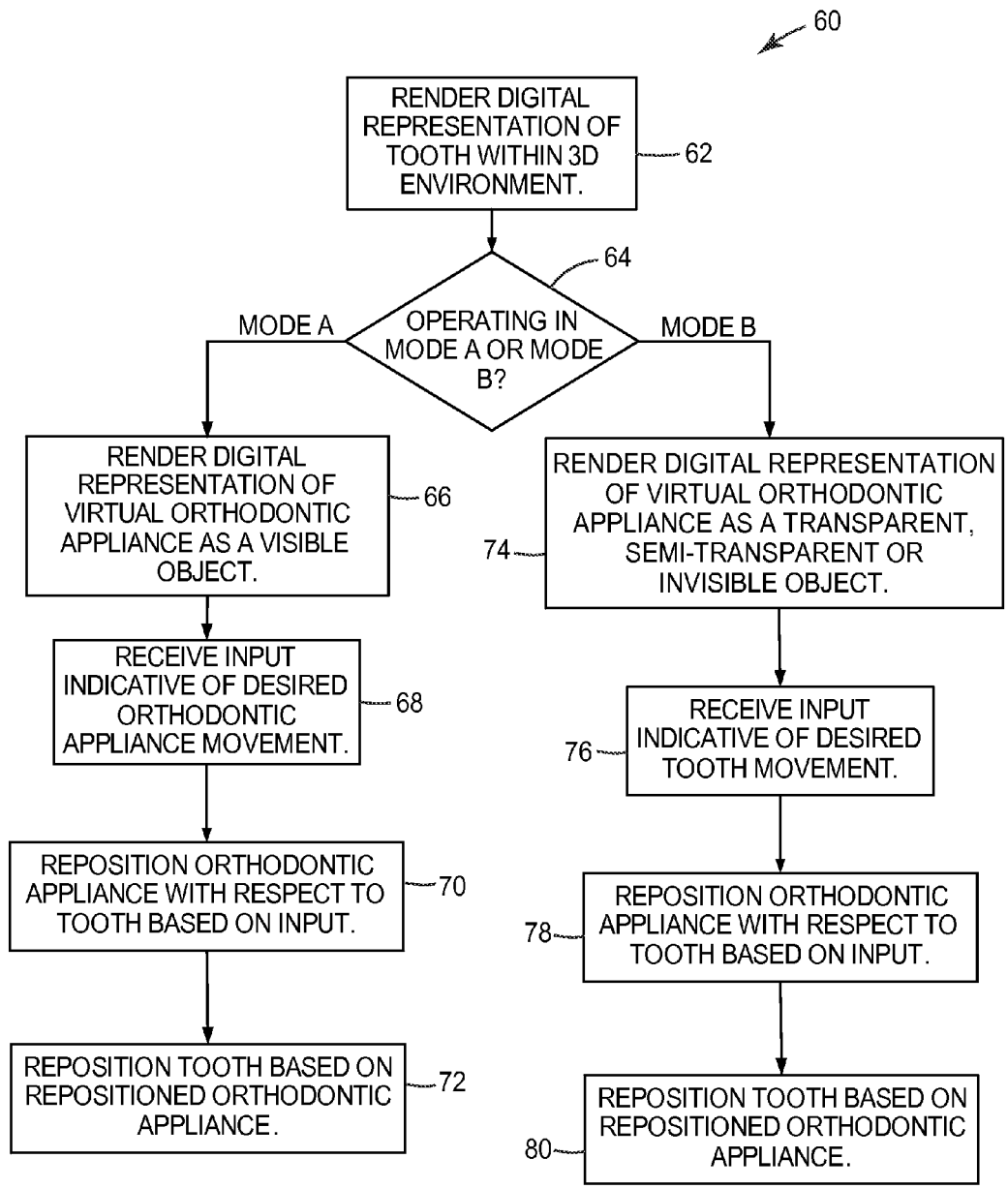
FIG. 3 is a flow diagram illustrating a process for generating an orthodontic treatment plan in accordance with the invention from the perspective of a system in accordance with the invention.

FIG. 3 is a flow diagram illustrating process 60 in accordance with the invention. Rendering engine 38 of modeling software 30 of client computing device 12 (FIG. 2) renders a digital representation of at least a part of one or more teeth within a 3D modeling environment (62). When operating in a first mode (labeled "Mode A" in FIG. 3 for clarity of description), rendering engine 38 may also render a digital representation of at least a part of an orthodontic appliance or a virtual orthodontic appliance (i.e., an object representative of the orthodontic appliance, which may behave as the orthodontic appliance behaves and/or include the same dimensions as the orthodontic appliance) as a visible object within the 3D modeling environment (64, 66). As described above, Mode A is useful for providing practitioner 14 with an interface in which practitioner 14 believes he or she is manipulating brackets (or another orthodontic appliance) in order to determine the proper placement of one or more brackets to achieve a desired functional and/or aesthetic result.

In Mode A, modeling software 30 receives input indicative of a desired movement for a bracket via user interface 32 (68). As described above, in a first mode, practitioner 14 selects one or more virtual brackets and directly manipulates the virtual bracket within the 3D environment to position the brackets with respect to respective teeth to achieve a desired functional and/or aesthetic result. After modeling software 30 receives the input indicative of the desired bracket movement from practitioner 14, orthodontic appliance control module 34 may reposition the bracket with respect to the corresponding tooth based on the input (70). Tooth control module 36 may then reposition the tooth in accordance with the repositioned bracket (72).

When operating in a second mode (labeled "Mode B" in FIG. 3 for clarity of description), rendering engine 38 may render a digital representation of the virtual orthodontic appliance as a transparent, semi-transparent or invisible object (64, 74). As described above, Mode B may be useful for providing practitioner 14 with a GUI that supports the perception that practitioner 14 is directly moving teeth, rather than brackets (or another orthodontic appliance). In Mode B, practitioner 14 may indicate the desired movement for a particular tooth by providing input via user interface 32 indicative of the desired movement for the tooth (76). As discussed above, user interface 32 is configured such that practitioner 14 believes he or she is directly manipulating the digital representation of the tooth within the 3D environment either by clicking and dragging the digital representation of the tooth within the 3D environment, inputting data indicative of a magnitude of movement in one or more directions or otherwise. However, practitioner 14 is not directly manipulating the tooth, but merely providing data (e.g., movement including magnitude and directional components) indicative of the desired tooth movement, which modeling software 30 (FIG. 2) then applies to a bracket associated with the tooth.

Orthodontic appliance control module 34 utilizes the data inputted by practitioner 14 to reposition the bracket (78). In particular, in one embodiment, orthodontic appliance control module 34 moves the bracket in a direction opposite to that inputted by practitioner 14, but the bracket movement generally has the same magnitude as the input from practitioner 14. In this way, orthodontic appliance control module 34 determines bracket placement that corresponds to practitioner's 14 input of the desired tooth position in order to generate an orthodontic therapy program that is customized for a particular patient. Tooth control module 36 then repositions the tooth based on the repositioned bracket (80).

Figure 4:
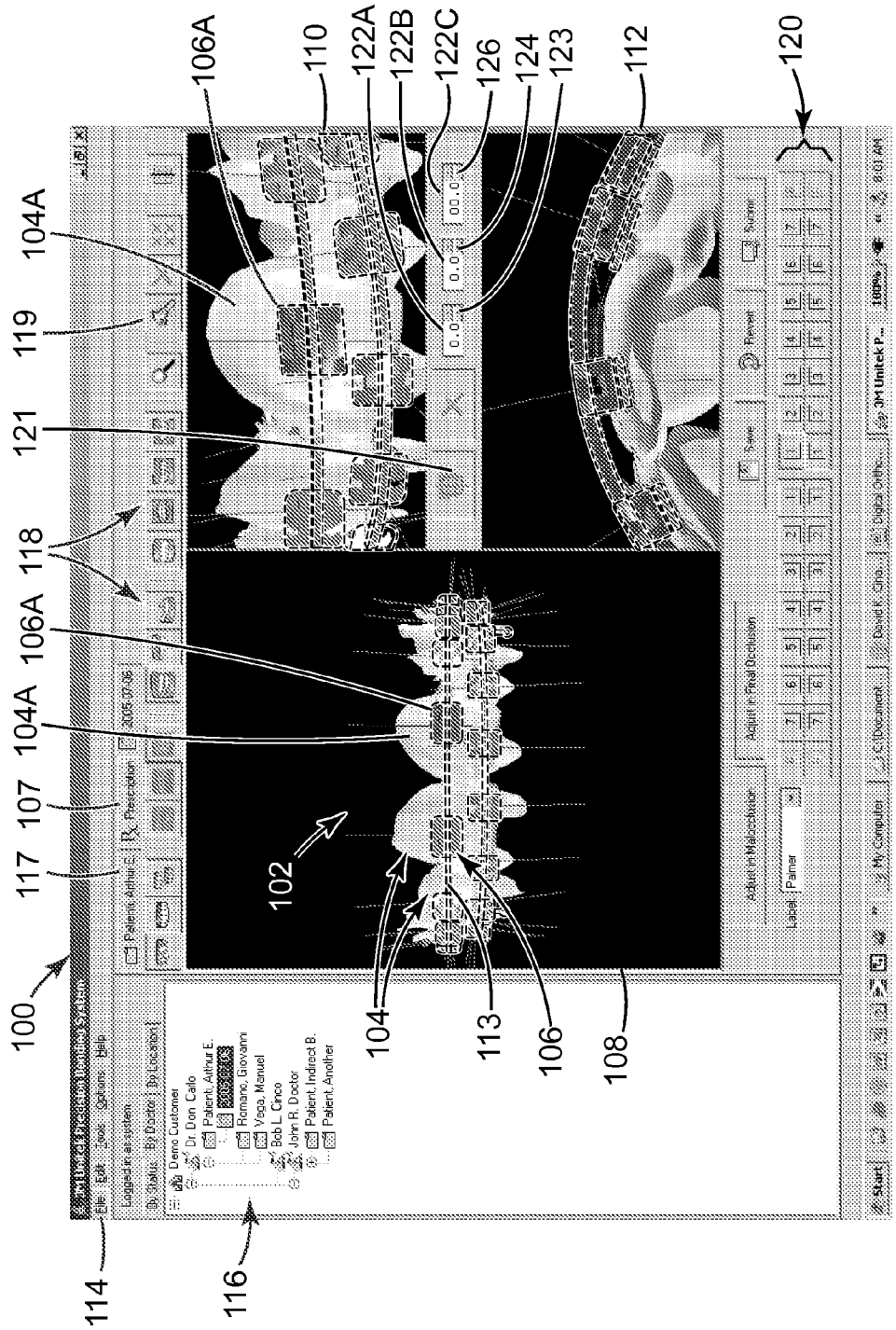
FIG. 4 is a display diagram of an exemplary user interface presented by modeling software in a first mode.

FIG. 4 is a display diagram of exemplary GUI 100 presented by modeling software 30. GUI 100 depicts a digital representation of dental arch 102 of a patient with a 3D modeling environment. Dental arch 102 includes a plurality of teeth 104, including tooth 104A. Also depicted in GUI 100 are digital representations of a plurality of transparent brackets 106 (indicated by phantom lines in FIG. 4) attached to teeth 104 of dental arch 102, including bracket 106A attached to tooth 104A. Thus, modeling software 30 is operating in a mode in which rendering engine 38 renders brackets 106 as transparent objects in GUI 100 (i.e., Mode B in FIG. 3). Alternatively, in Mode B, brackets 106 may be rendered as invisible objects (i.e., not rendered). The type of brackets 106 and starting positions (e.g., an occlusal-gingival height and a mesial-distal position) of brackets 106 with respect to teeth 104 may be preselected by default or preselected by practitioner 14 or another technician and stored within prescription page 107, which may also include other textual information regarding the bracket selection and other prescriptive data. For example, client computing device 12 may be configured to allow practitioner 14 to specify an initial placement position of one or more brackets 106 on a respective tooth 104.

GUI 100 allows practitioner 14 to choose from any of several views of a patient's dentition. In the embodiment of GUI 100 illustrated in FIG. 4, GUI 100 depicts three views: display area 108 depicts an entire dental arch 102, while display area 110 depicts an enlarged view of a portion of dental arch 102, and display area 112 depicts a top perspective view of a portion of dental arch 102.

Orthodontic appliance control module 34 and tooth control module 36 (FIG. 2) enable practitioner 14 to interactively develop a treatment plan and corresponding orthodontic prescription which will result in a desired final occlusion using the virtual 3D model of the patient's dentition presented on GUI 100. GUI 100 may present the crowns and/or the roots or gingiva of the teeth to the practitioner 14 for visualization and interactive movement of teeth 104.

In the illustrated embodiment of FIG. 4, GUI 100 includes a menu input area 116 by which a user, e.g., practitioner 14, may access patient data 46 for a particular patient 16. In the embodiment shown in FIG. 4, practitioner 14 (or another user) may select a patient file from within patient data 46 via menu input area 116. After selecting a particular patient file, GUI 100 displays patient data page 117, which may include data relating to the selected patient, such as notes reflecting practitioner's 14 observations relating to the selected patient's reaction to an orthodontic treatment. Practitioner 14 may also input data to patient data page 117.

GUI 100 provides selection buttons 118 by which practitioner 14 can selectively enable and disable the rendering and display of any of several different views of the patient's dental arch within the display areas 108, 110, and 112, including various perspective views, various composite views (illustrating more than one perspective view), dental arch 102 in an untreated state or a treated state, and so forth. In addition, GUI 100 provides measuring tool 119, which enables a user to measure between two points, such as two user-selected points.

Practitioner 14 may specify the desired movement or placement of one or more teeth 104 (and in some embodiments, brackets 106) by interacting with GUI 100. Practitioner 14 may select tooth 104A by, for example, pointing and clicking a peripheral device on the digital representation of tooth 104A or selecting tooth 104A from dental arch 102 by selecting a button associated with the particular tooth from object selection menu 120. The discussion below in reference to tooth 104A is merely exemplary and in practice, practitioner 14 may select any of teeth 104 to manipulate. In the embodiment shown in FIG. 4, object selection menu 120 identifies particular teeth 104 in dental arch 102 using the Palmer Notation System. In alternate embodiments, object selection menu may identify individual teeth 104 and/or brackets 106 by other suitable numbering or labeling systems, such as the Universal Numbering System or the International Numbering System. Practitioner 14 may also activate the interactive features of GUI 100 and modeling software 30 by clicking or otherwise selecting activation box 121.

Practitioner 14 may indicate a desired position for selected tooth 104A by, for example, clicking and dragging tooth 104A to a specified point within the 3D environment, by manually entering a metric indicative of the desired point on virtual archwire 113 (shown in phantom lines), etc. Alternatively, practitioner 14 may specify a desired position for tooth 104A or indicate a desired movement for tooth 104A by inputting a magnitude of movement via navigation input boxes 122A, 122B, and 122C (collectively "navigation input boxes 122"). In first navigation input box 122A, practitioner 14 may input a number representative of the magnitude of movement of tooth 104A in the occlusal-gingival direction. Alternatively, practitioner 14 may use arrows 123 to input the magnitude of movement. In second navigation input box 122B, practitioner 14 may input a number representative of the magnitude of movement of tooth 104A in the mesial-distal direction. Alternatively, practitioner 14 may use arrows 124 to input the magnitude of movement. In third navigation input box 122C, practitioner 14 may input a number representative of the magnitude of angulation of tooth 104A about a labial-lingual axis. Alternatively, practitioner 14 may use arrows 126 to input the magnitude of angulation.

In some embodiments, practitioner 14 may indicate movement of more than one tooth 104 at a time, such as by selecting more than one tooth from selection menu 120 and dragging the selected teeth to the desired positions.

In some embodiments, GUI 100 may also include icons and/or graphical devices superimposed on the digital representations of dental arch 102 within one or more display areas 108, 110 or 112 that enable a user to manipulate dental arch 102 and simulate the movement of specified teeth 104 relative to other teeth 104 within the 3D environment. While specification of a position of one or more teeth 104 is described herein, it should be understood that software 30 may include more than one operating mode, as described above, and in one of the operating modes, a position of one or more brackets 106 may be specified.

Figure 5:
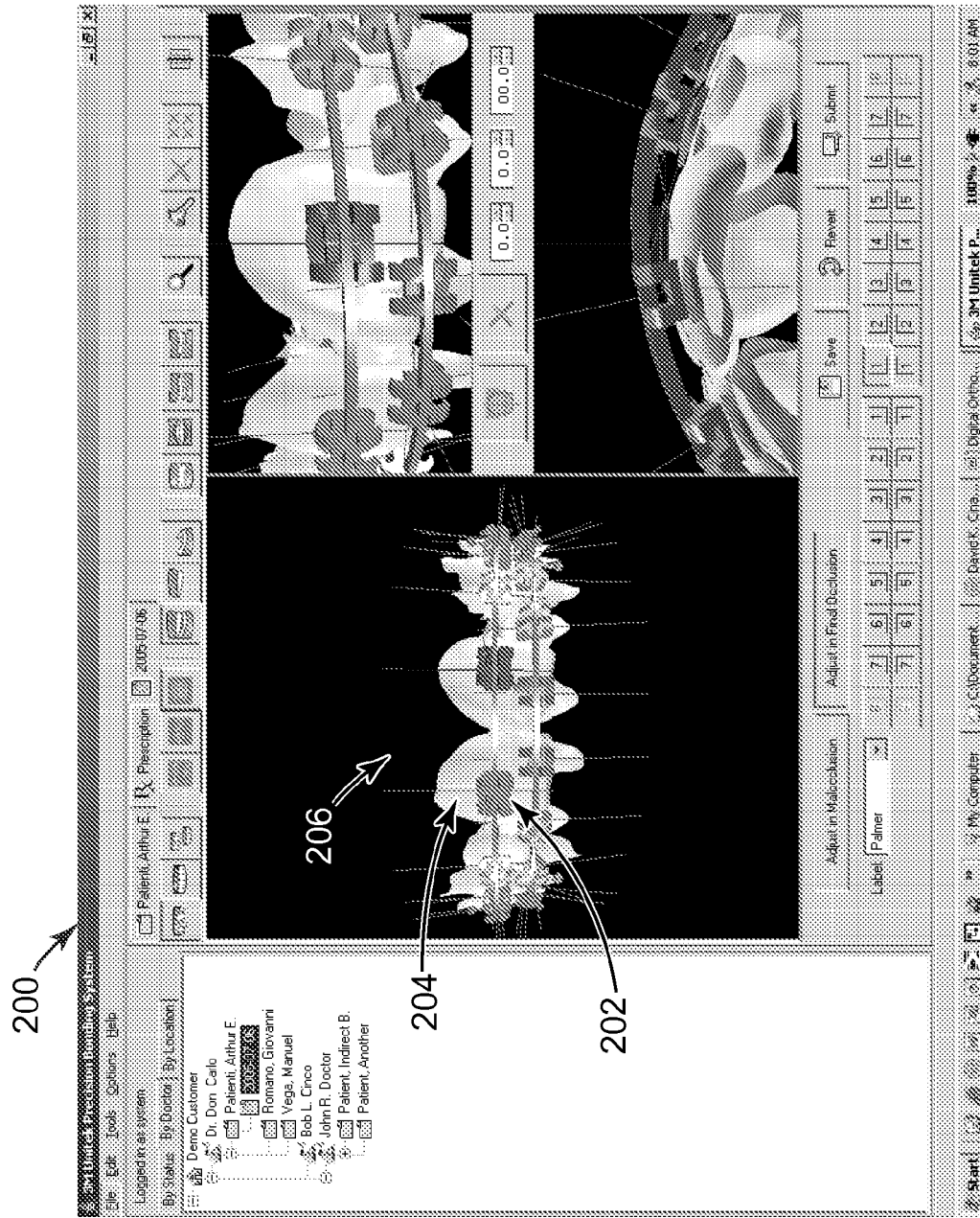
FIG. 5 is a display diagram of a second mode of the user interface of FIG. 4.

FIG. 5 is a display diagram of another exemplary GUI 200 presented by modeling software 30 in another operating mode (Mode A in FIG. 3), in which brackets 202 are rendered as visible objects. GUI 200 is substantially similar to GUI 100 of FIG. 4 except that brackets 202 are rendered as visible objects. As previously described in reference to FIG. 3, in Mode A, practitioner 14 may directly manipulate one or more brackets 202 in order to select a position of brackets 202 with respect to teeth 204 that results in a desired functional and/or aesthetic result.

In an embodiment in which modeling software 30 includes two or more modes, practitioner 14 may select between the modes from a pull-down menu from along menu-bar 114 or menu input area 116. For example, practitioner 14 may select between Modes A and B (FIG. 3). In Mode A, client computing device 12 (FIGS. 1 and 2) controls GUI 200 (FIG. 5) of modeling software 30 such that practitioner 14 may directly manipulate one or more visibly rendered brackets 202 to achieve the positions of teeth 204 and determine a final position of one or more orthodontic appliances for achieving a desired functional and/or aesthetic result for dental arch 206.

In another Mode B, client computing device 12 (FIGS. 1 and 2) controls GUI 100 (FIG. 4) of modeling software 30 to provide practitioner 14 with a perception that he or she is directly manipulating one or more teeth 104 in order to specify final tooth positions, while in fact, modeling software 30 applies the movements inputted by practitioner 14 via GUI 100 to brackets 106. However, modeling software 30 effectively moves virtual brackets and computes tooth positions in the same manner for both modes. Alternatively, modeling software 30 may include other operating modes, such as an operating mode in which practitioner 14 may manipulate both teeth 104 and corresponding brackets 106.

The invention described herein is useful for interactively creating a treatment plan for a patient. Various embodiments of the invention have been described. These and other embodiments are within the scope of the following claims.

The invention claimed is:

1. A computer-implemented method comprising:
rendering a digital representation of at least a portion of a tooth within a three-dimensional (3D) environment and displaying the digital representation via a user interface of a computing device;
receiving input, via the user interface of the computing device, indicative of a desired movement for the tooth, wherein the input specifies a movement in a direction of the desired movement for the tooth within the 3D environment;
prior to moving the tooth within the 3D environment based on the input, calculating a new appliance position for a virtual appliance in response to the input instead of moving the tooth within the 3D environment in direct response to the input;
calculating a new tooth position for the tooth based on the new appliance position of the virtual appliance; and
rendering the digital representation of the at least a portion of the tooth at the new tooth position within the 3D environment.

2. The method of claim 1, wherein the input defines a first movement within the 3D environment, and the method further comprises:
calculating a second movement within the 3D environment based on the first movement, wherein the second movement is substantially equal in magnitude to the first movement and in a substantially opposite direction, wherein calculating the new appliance position for the virtual appliance in response to the input comprises calculating the new appliance position based on the second movement.

3. The method of claim 2, wherein the first movement is constrained within geometric parameters dictated by a virtual archwire.

4. The method of claim 3, wherein the first movement is constrained to movement along the virtual archwire.

5. The method of claim 3, wherein the first movement is constrained to movement generally perpendicular to the virtual archwire, generally perpendicular being generally in an occlusal-gingival direction.

6. The method of claim 3, wherein the first movement is constrained to rotation about a labial-lingual axis.

7. The method of claim 1, wherein receiving input indicative of the desired movement for the tooth comprises receiving input from a user indicating a desired movement for the tooth via a user interface.

8. The method of claim 7, wherein the user interacts with the user interface to indicate the desired movement for the tooth by providing input comprising clicking and dragging the tooth within the 3D environment, and wherein calculating the new appliance position for the virtual appliance comprises, prior to moving the tooth within the 3D environment based on the input, applying the desired movement indicated by the clicking and dragging to the virtual appliance instead of the tooth to calculate the new appliance position.

9. The method of claim 8, wherein the dragging of the tooth by the user is constrained within geometric parameters determined by at least one of the behavior or dimensions of the virtual appliance within the 3D environment.

10. The method of claim 7, wherein the user interacts with the user interface by inputting metrics indicative of a magnitude of the desired movement for the tooth.

11. The method of claim 1, wherein the virtual appliance is a bracket and the method further comprises moving the bracket to the new appliance position on a surface of the tooth within the 3D environment.

12. The method of claim 1, and further comprising displaying the digital representation of the virtual appliance as a substantially transparent object within the 3D environment.

13. The method of claim 12, wherein the digital representation of the virtual appliance is displayed as the substantially transparent object within the 3D environment in a first operating mode, and in a second operating mode, the virtual appliance is displayed as a visible object.

14. The method of claim 1, wherein rendering a digital representation of a tooth comprises rendering a digital representation of a dental arch, and the method further comprises automatically calculating adjusted positions for affected teeth of the dental arch as a consequence of the new tooth position of the tooth.

15. The method of claim 1, and further comprising displaying a digital representation of a virtual archwire within the 3D environment.

16. The method of claim 15, wherein the digital representation of the virtual archwire is displayed as a substantially transparent object within the 3D environment.

17. The method of claim 1, wherein the direction of the desired movement for the tooth comprises a first direction and calculating the new appliance position comprises applying the input indicative of the desired movement for the tooth to the orthodontic appliance, rather than the tooth, in a second direction that is opposite the first direction.

18. A system comprising:
a computing device; and
modeling software executing on the computing device, wherein the modeling software comprises:
a rendering engine that renders a digital representation of at least a portion of a tooth within a three-dimensional (3D) environment;
a user interface to receive user input indicating a desired movement for the tooth, wherein the user input specifies a movement in a direction of the desired movement for the tooth within the 3D environment;
an orthodontic appliance control module to automatically calculate an orthodontic appliance position based on the input prior to moving the tooth within the 3D environment based on the input; and
a tooth control module to calculate a new tooth position of the tooth within the 3D environment in accordance with the orthodontic appliance position.

19. The system of claim 18, wherein the user interface displays the digital representation of at least a portion of the tooth at the new tooth position.

20. The system of claim 18, wherein the orthodontic appliance control module automatically calculates an orthodontic appliance position by applying the input indicative of a desired movement for the tooth to the orthodontic appliance rather than the tooth.

21. The system of claim 18, wherein the rendering engine renders a digital representation of the orthodontic appliance.

22. The system of claim 18, wherein the user input defines a first movement within the 3D environment, and the orthodontic appliance control module is configured to calculate a second movement within the 3D environment based on the first movement, wherein the second movement is substantially equal in magnitude to the first movement and in a substantially opposite direction along an virtual archwire than the first movement, and the orthodontic appliance control module calculates the orthodontic appliance position using the second movement.

23. The system of claim 18, wherein a user provides the user input via one or more incremental movements of a peripheral device of the user interface.

24. The system of claim 23, wherein the user interface provides the user with a perception that the user is moving the tooth within the 3D environment with the peripheral device as the user interacts with the user interface to provide the user input indicating a desired movement for the tooth.

25. The system of claim 18, wherein a user provides the user input by inputting metrics indicative of a magnitude of the desired movement for the tooth via the user interface.

26. The system of claim 18, wherein the orthodontic appliance is a bracket and the orthodontic appliance control module is configured to move the bracket to the orthodontic appliance position within the 3D environment, the orthodontic appliance position being on a surface of the tooth.

27. The system of claim 21, wherein the digital representation of the orthodontic appliance is at least partially transparent.

28. The system of claim 18, wherein the rendering engine renders a digital representation of a virtual archwire.

29. The system of claim 18, the modeling software comprising:
a first operating mode, wherein the user interface is configured to receive user input indicating the desired position for the tooth; and
a second operating mode different than the first operating mode, wherein in the second operating mode, the user interface is configured to receive user input indicating a desired orthodontic appliance position, the orthodontic appliance control module is configured to move the orthodontic appliance to the desired orthodontic appliance position based on the input, and the tooth control module is configured to automatically calculate an adjusted position for the tooth based on the desired orthodontic appliance position.

30. A computer-readable medium comprising instructions for causing a programmable processor to:
render a digital representation of at least a portion of a tooth within a three-dimensional (3D) environment;
render a virtual orthodontic appliance as a transparent or semi-transparent object within the 3D environment;
receive input indicative of a desired movement for the tooth, wherein the input specifies a movement in a direction of the desired movement for the tooth within the 3D environment;
prior to moving the tooth within the 3D environment, calculate a new position for the virtual orthodontic appliance in response to the input; and
calculate a new position for the tooth within the 3D environment based on the new position of the virtual orthodontic appliance.

31. The computer-readable medium of claim 30, and further comprising instructions for causing the programmable processor to display the digital representations of at least a portion of the tooth and the virtual orthodontic appliance at their respective new positions.

* * * * *